United States Patent [19]

Dolle et al.

[11] Patent Number: 5,670,494
[45] Date of Patent: Sep. 23, 1997

[54] N-(PYRIMIDINYL)-ASPARTIC ACID ANALOGS AS INTERLEUKIN-1β CONVERTING ENZYME INHIBITORS

[75] Inventors: Roland E. Dolle, King of Prussia; Catherine P. Prouty, Doylestown, both of Pa.; Prasad V. Chaturvedula, Cheshire, Conn.; Stanley J. Schmidt, Chester Springs, Pa.

[73] Assignee: Sanoft, Paris Cedex

[21] Appl. No.: 559,870

[22] Filed: Nov. 20, 1995

Related U.S. Application Data

[63] Continuation-in-part of Ser. No. 221,712, Mar. 31, 1994, abandoned.

[51] Int. Cl.$^6$ .................. A61K 31/675; A61K 31/505; C07D 239/22; C07F 9/6512
[52] U.S. Cl. .................. 514/86; 514/269; 544/243; 544/319
[58] Field of Search .................. 544/243, 319; 514/86, 269

[56] References Cited

U.S. PATENT DOCUMENTS 5,441,960  8/1995  Bernstein et al. .................. 514/269

OTHER PUBLICATIONS

Bernstein et al, *Chemical Abstracts*, vol. 119, No. 72617 (1993).
Bernstein et al, *Chemical Abstracts*, vol. 120, No. 217713 (1994).
Veale et al, *J. Med. Chem.* 38, pp. 98–108 (1995).
Miller et al, *The Lancet*, vol. 341, pp. 146–148 (1993).
Cominelli et al, *J. Clin. Invest.* 86, pp. 972–980 (1990).
Schwab et al., *Infect. Immun.* 59 pp. 4436–4442 (1991).
Estrov et al, *Blood*, vol. 78, pp. 1476–1484 (1991).
Estrov et al, *Blood*, vol. 79, pp. 1938–1945 (1992).

*Primary Examiner*—Emily Bernhardt
*Attorney, Agent, or Firm*—William J. Davis; Imre Balogh

[57] ABSTRACT

Disclosed are compounds, compositions and methods for inhibiting interleukin-1β (1L-β) protease activity. The compounds, N-(pyrimidinyl)-aspartic acid α-substituted methyl ketones and aspartic acid aldehydes, have the formula (I) set out herein.

These compounds are inhibitors of 1β-converting enzyme and as such are useful whenever such inhibition is desired. For example, they may be used as research tools in pharmacological, diagnostic and related studies and in the treatment of diseases in mammals in which IL-β protease activity is implicated.

2 Claims, No Drawings

N-(PYRIMIDINYL)-ASPARTIC ACID ANALOGS AS INTERLEUKIN-1β CONVERTING ENZYME INHIBITORS

This application is a continuation-in-part of application Ser. No. 08/221,712, filed Mar. 31, 1994, now abandoned.

BACKGROUND OF THE INVENTION

1. Field of the Invention

This invention relates to a series of novel aspartic acid analogs which exhibit selective in vitro and in vivo inhibition of interleukin-1β converting enzyme, to compositions containing the novel aspartic acid analogs and to methods for therapeutic utility. More particularly, the interleukin-1β converting enzyme inhibitors described in this invention comprise novel N-(pyrimidinyl)-aspartic acid aldehydes and α-substituted methyl ketones which possess particular utility in the treatment of inflammatory and immune-based diseases of lung, central nervous system, kidneys, joints, eyes, ears, skin, gastrointestinal tract, urogenital system and connective tissues.

2. Reported Developments

Interleukin-1β (IL-1β) protease (also known as interleukin-1β converting enzyme or ICE) is the enzyme responsible for processing of the biologically inactive 31 kD precursor IL-1β to the biologically active 17 kD form (Kostura, M. J.; Tocci, M. J.; Limjuco, G.; Chin, J.; Cameron, P.; Hillman, A. G.; Chartrain, N. A.; Schmidt, J. A., *Proc. Nat. Acad. Sci.*, (1989), 86, 5227–5231 and Black, R. A.; Kronheim, S. R.; Sleath, P. R., *FEBS Let.*, (1989), 247, 386–391). In addition to acting as one of the body's early responses to injury and infection, IL-1β has also been proposed to act as a mediator of a wide variety of diseases, including rheumatoid arthritis, osteoarthritis, inflammatory bowel disease, sepsis, acute and chronic myelogenous leukemia and osteoporosis (Dinarello, C. A.; Wolff, S. M., *New Engl. J. Med.*, (1993), 328, 106). A naturally occurring IL-1β receptor antagonist has been used to demonstrate the intermediacy of IL-1β in a number of human diseases and animal models (Hannum, C. H.; Wilcox, C. J.; Arend, W. P.; Joslin, G. G.; Dripps, D. J.; Heimdal, P. L.; Armes, L. G.; Sommer, A.; Eisenberg, S. P.; Thompson, R. C., Nature, (1990), 343, 336–340; Eisenberg, S. P.; Evans, R. J.; Arend, W. P.; Verderber, E.; Brewer, M. T.; Hannum, C. H.; Thompson, R. C., Nature (1990), 343, 341–346; Ohlsson, K.; Bjork, P.; Bergenfeldt, M.; Hageman, R.; Thompson, R. C., *Nature*, (1990), 348, 550–552; Wakabayashi, G., *FASEB*, (1991), 338–343; Pacifici, R.; et al. *Proc. Natl. Acad. Sci.* (1989), 86, 2398–2402 and Yamamoto, I.; et al. *Cancer Rsh* (1989), 49, 4242–4246). The specific role of IL-1β in inflammation and immunomodulation is supported by the recent observation that the cowpox virus employs an inhibitor of ICE to suppress the inflammatory response of its host (Ray, C. A. et al, *Cell*, (1992), 69,597–604).

In summary, the utility of ICE inhibitors in modifying certain IL-1β mediated disease states has been suggested and demonstrated in vivo by several workers in the field. The following review of the current state of the art in ICE research further supports such utility of ICE inhibitors:

1) WO 9309135, published May 11, 1993, teaches that peptide-based aspartic acid arylacyloxy-and aryoxymethyl ketones are potent inhibitors of ICE in vitro. These compounds also specifically inhibited ICE in the whole cell (in vivo) by their ability to inhibit the formation of mature IL-1β in whole cells. These ICE inhibitors also demonstrated utility in reducing fever and inflammation/swelling in rats.

2) Patients with Lyme disease sometimes develop Lyme arthritis. *B. burgdorferi*, the causative agent of Lyme disease, is a potent inducer of IL-1 synthesis by mononuclear cells. Miller et al. (Miller, L. C.; Lynch, E. A. Isa, S.; Logan, J. W.; Dinarello, C. A.; and Steere, A. C., "Balance of synovial fluid IL-1β and IL-1 Receptor Antagonist and Recovery from Lyme arthritis", *Lancet* (1993) 341; 146–148) showed that in patients who recovered quickly from Lyme Arthritis, the balance in synovial fluid of IL-1-beta and IL-1 ra was in favor of IL-ra. When the balance was shifted in favor of IL-1β, it took significantly longer for the disease to resolve. The conclusion was that the excess IL-1ra blocked the effects of the IL-1β in the patients studied.

3) IL-1 is present in affected tissues in ulcerative colitis in humans. In animal models of the disease, IL-1β levels correlate with disease severity. In the model, administration of 1L-1ra reduced tissue necrosis and the number of inflammatory cells in the colon. See, Cominelli, F.; Nast, C. C.; Clark, B. D.; Schindler, R., Llerena, R.; Eysselein, V. E.; Thompson, R. C.; and Dinarello, C. A.; "Interleukin-1 Gene Expression, Synthesis, and Effect of Specific IL-1 Receptor Blockade in Rabbit Immune Complex Colitis" *J. Clin. Investigations* (1990) Vol. 86, pp, 972–980.

4) IL-1ra supresses joint swelling in the PG-APS model of arthritis in rats. See Schwab, J. H.; Anderle, S. K.; Brown, R. R.; Dalldorf, F. G. and Thompson, R. C., "Pro- and Anti-Inflammatory Roles of Interelukin-1 in Recurrence of Bacterial Cell Wall-Induced Arthritis in Rats". *Infect. Immun.* (1991 ) 59; 4436–4442.

5) IL-1ra shows efficacy in an small open-label human Rheumatoid Arthritis trial. See, Lebsack, M. E.; Paul, C. C.; Bloedow, C. C.; Burch, F. X.; Sack, M. A.; Chase, W., and Catalano, M. A. "Subcutaneous IL-1 Receptor Antagonist in Patients with Rheumatoid Arthritis", *Arth. Rheum.* (1991 ) 34; 545.

6) IL-1 appears to be an autocrine growth factor for the proliferation of chronic myelogenous leukemia cells. Both IL-1ra and sIL-1R inhibit colony growth in cells removed from leukemia patients.
See, Estrov, Z.; Kurzrock, R.; Wetzler, M.; Kantarjian, H.; Blake, M.; Harris, D.; Gutterman, J. U.; and Talpaz, M., "Supression of Chronic Myelogenous Leukemia Colony Growth by Interleukin-1 (IL-1) Receptor Antagonist and Soluble IL-1 Receptors: a Novel Application for Inhibitors of IL-1 Activity". *Blood* (1991 ) 78; 1476–1484.

7) As in 6) above, but for acute myelogenous leukemia rather than chronic myelogenous leukemia.
See, Estrov, Z.; Kurzrock, R.; Estey, E.; Wetzler, M.; Ferrajoli, A.; Harris, D.; Blake, M.; Guttermann, J. U.; and Talpaz, M. "Inhibition of Acute Myelogenous Leukemia Blast Proliferation by Interleukin-1 (IL-1) Receptor Antagonist and Soluble IL-1 Receptors". (1992) *Blood* 79; 1938–1945.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive 5,670,494 to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis.

All of the inhibitors of ICE described in the art known to Applicants are peptide-based, taking advantage of the substrate specificity of the enzyme. We describe in this invention non-peptide based inhibitors of ICE, specifically where the pyrimidine serves as a recognition surrogate for the P2 and P3 amino acids which up until now had to be present to yield a potent ICE inhibitor (see structure 1). One well-known advantage of non-peptide inhibitors versus their peptide counterpart is that in vivo metabolism and excretion of such non-peptidic agents to greatly attenuated, thereby leading to enhanced bioavailability of these compounds in animals and humans (Humphrey, M. J. and Ringrose, P. S., "Peptides and Related Drugs: A Review of Their Absorption, Metabolism, and Excretion", *Drug Metabolism Reviews*, (1986), 17, 283–310. Also Plattner, J. J. and Norbeck, D. W. "Obstacles to Drug Development from Peptide Leads", *Drug Discovery Technologies*, (1990), Chapter 5, 92–126, C. R. Clark and W. H. Moos, eds.; Horwood: Chichester, U.K.

Structure 1

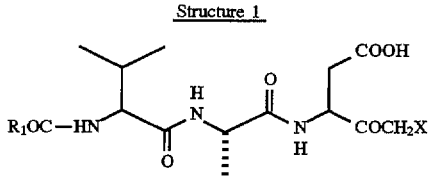

Peptide-based ICE inhibitor
(Dolle, R. et al; J. Med. Chem.(1994), 37, 563)

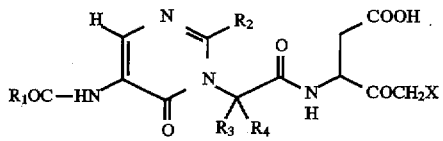

Pyrimidine-based ICE inhibitor
(this invention)

It should be noted that the pyrimidine-based trifluoromethyl ketones (structure 2) were recently described as inhibitors of the serene protease, elastase. Since ICE is a cysteine protease and it is known in the prior art that trifluoromethyl ketones are rather poor inhibitors of cysteine proteases (See, Imperialia, B. and Abies, R. H., *Biochemistry*. (1986), 25, 3760–7), it is expected that the pyrimidines of FIG. 2 would not be inhibitors of ICE. Also, it is known that ICE requires the aspartic acid side chain (—CH$_2$COOH) at PI. Pyrimidines which inhibit elastase (FIG. 2) contain the valine side chain (—CHMe$_2$). In addition, as will be shown later, the pyrimidine-based ICE inhibitors (Structure 1) described in this invention do not inhibit human leucocyte elastase and hence are exquisitely selective for ICE and distinct from the known elastase inhibitors.

Structure 2

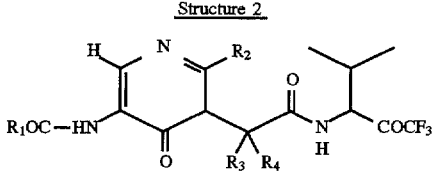

-continued
Structure 2

Pyrimidine-based elastase inhibitor
(Imperical Chemical Industries;
EPO 528 633 A1; 1993)

SUMMARY OF THE INVENTION

Compounds of formula I have been found to be potent inhibitors of interleukin-1β converting enzyme (ICE). Compounds of formula I are useful in the treatment of diseases including inflammation in lung, central nervous system, kidney, joints, eyes, ears, skin, gastrointestinal tract and connective tissues.

According to the present invention, there is provided a compound of the formula (I) or a pharmaceutically acceptable salt thereof.

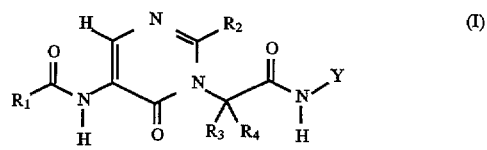

(I)

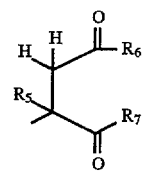

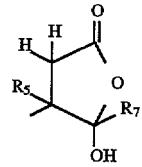

$R_5$ is H or deuterium;

$R_6$ is $OR_8$ or NHOH where $R_8$ is independently H, alkyl, or aralkyl $R_3$ and $R_4$=independently H, alkyl or aralkyl $R_2$=H, alkyl, —(CH$_2$)$_{0-4}$-cycloalkyl,

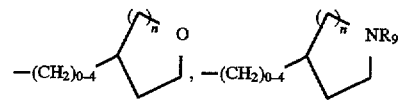

aryl, heteroaryl, aralkyl, heteroaralkyl, —(CH$_2$)$_{2-4}$—R$_{10}$;
where n=1–3;
where R$_{10}$=alkoxy, CH$_2$F, CHF$_2$, CF$_3$, CF$_2$CF$_3$, OH, COOR$_{11}$, CONR$_9$R$_{11}$, or NR$_8$R$_{11}$;
where R$_9$ is independently H, alkyl, aryl, aralkyl, heteroaryl, heteroaralkyl, —CH$_2$CH$_2$O-alkyl and C(O)—R$_{12}$;

where R$_{11}$ is independently H, alkyl, aryl, aralkyl, heteroaryl and heteroaralkyl;
and when R$_9$ and R$_{11}$ are taken together, they can equal a five, six or seven membered ring of the type:

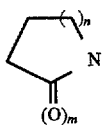

where n=1–3 and m=0–1; and $R_{12}$ is alkyl, aryl, aralkyl, heteroaryl and heteroaralkyl;

$R_7=$H, $CH_2F$, $CHR_{13}O(CO)_{0-1}$-aryl, $CHR_{13}OP(O)(R_{14})R_{(15)}$

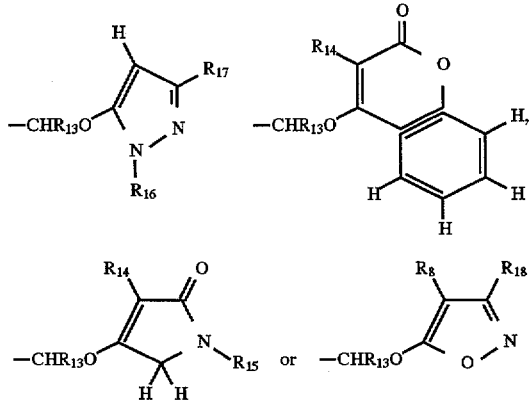

wherein:
$R_{13}$=H or alkyl
$R_{14}$=H, alkyl or aryl
$R_{15}$=H, alkyl or aryl
$R_{16}$=H, alkyl, aryl, heteroaryl, aralkyl or heteroaralkyl
$R_{17}$=H, alkyl, $CF_3$, $CF_2CF_3$, aryl, heteroaryl, aralkyl, heteroaralkyl, $COOR_{11}$, or $CONR_9R_{11}$
$R_{18}$=H, alkyl, $CF_3$, $CF_2CF_3$, aryl, heteroaryl, aralkyl, heteroaralkyl
$R_1$ is defined as:
$R_{19}-R_2$, $R_{19}-R_{20}$, $R_{19}-R_{21}$, $R_{19}-NR_9R_{11}$
where $R_{19}=(CR_3R_4)_{0-4}$;
$R_{20}=$

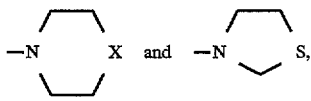

where X=O, S, $NR_9$
$R_{21}=$

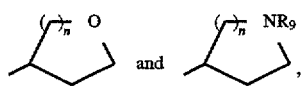

where n=1–3; $R_{22}O$—
where $R_{22}$—alkyl, aryl, heteroaryl, aralkyl, heteroaralkyl, $R_{19}$-cycloalkyl, $R_{19}-R_{21}$, $R_{23}-R_{10}$, $R_{23}-R_{20}$;
wherein $R_{23}=(CR_3R_4)_{2-4}$;
$R_9 R_{11}N$— and $R_{24}R_{11}N$—
where $R_{24}=R_{19}$-cycloalkyl, $R_{19}-R_{21}$, $R_{23}-R_{10}$, $R_{23}-R_{20}$, $CR_3R_4COOR_{11}$ and $CR_3CR_4CONR_9R_{11}$;

As used herein, the term "pharmaceutically acceptable salts" include the acid and base addition salts.

The term "acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

As employed above and throughout the disclosure, the following terms, unless otherwise indicated, shall be understood to have the following meanings:

"Alkyl" is defined as a saturated aliphatic hydrocarbon which may be either straight- or branched-chain. Preferred groups have no more than about 12 carbon atoms and may be methyl, ethyl, propyl, and so on and structural isomers of propyl, butyl, pentyl, hexyl, octyl, nonyl, decyl, undecyl, dodecyl.

"Cyclolalkyl" is defined as a saturated cyclic aliphatic hydrocarbon containing from at least 3 to as many as 8 carbon atoms. Preferred groups include cyclopropyl, cyclobutyl, cyclopentyl, cyclohexyl, cycloheptyl and cyclooctyl.

"Aryl" is defined as a phenyl or naphthyl ring or a substituted phenyl or naphthyl ring wherein one or more of the hydrogen atoms has been replaced by the same or different substituents as selected from $R_1$, $COR_1$, or $R_{25}$, where $R_{25}$ is defined as H, OH, halo, —$OC(O)R_{11}$, —$C(O)R_{11}$, —$NR_{11}C(O)R_1$, $NR_{11}C(O)(CR_3R_4)_{2-6}R_1$, —$COOR_{11}$, —$COOR_{11}$, —$CONR_9,R_{11}$, $R_{11}S$—, —$NR_9,R_{11}SO_2R_8$, —$SO_2NR_9,R_{11}$, nitro, cyano, —$NR_{11}CONR_9,R_{11}$, where $R_1,R_8$, $R_9,R_{11}$, and $R_{12}$, are defined as above.

"Heteroaryl" is defined as an unsubstituted or an optionally substituted mono- or bicyclic ring system of about 5 to about 12 carbon atoms and where each monocyclic ring may possess from 0 to about 4 heteroatoms, and each bicyclic ring my possess about 0 to about 5 heteroatoms selected from N, O, and S provided said heteroatoms are not vicinal oxygen and/or sulfur atoms and where the substituents, numbering from 0 to about 5 may be located at any appropriate position of the ring system and are optionally selected from the substituents listed for those described for aryl. Examples of such mono- and bicyclic ring systems which are by no means meant to limit the scope of this invention, including benzofuran, benzothiophene, indole, benzopyrazole, coumarin, isoquinoline, pyrrole, thiophene, furan, thiazole, imidazole, pyrazole, triazole, quinoline, pyrollidenone, pyrimidine, pyridine, pyridone, pyrazine, pyridazine, isothiazole, isoxazole and tetrazole.

"Aralkyl" refers to an alkyl group substituted by an aryl radical. For example, benzyl.

"Heteroaralkyl" refers to an alkyl group substituted by a heteroaryl radical. For example, (4-pyridyl)methyl.

"Alkoxy" refers to an O-atom substituted by an alkyl, aryl or aralky radical. For example methoxy, ethoxy, phenoxy, benzyloxy.

"Halo" means iodo, bromo, chloro, and fluoro.

The designation "$(CR_3R_4)_{2-4}$" refers to an alkyl linkage composed of at least 2 but not more than 4 carbon atoms where said carbon atoms are independently substituted with radicals described by $R_3$ and $R_4$. Examples of such linkages include but are not limited to ethyl, propyl, butyl, 2-methylethyl (—$(MeHCCH_2$—), 2,2-dimethylethyl ($Me_2CCH_2$—).

The present invention also concerns the pharmaceutical composition and method of treatment of IL-1β protease mediated disease states or disorders in a mammal in need of such treatment comprising the administration of IL-1β protease inhibitors of formula (I) as the active agent. These disease states and disorders include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, immune-based disease, such as hypersensitivity; auto-immune diseases, such as multiple sclerosis; bone diseases; and certain tumors and leukemias.

The present invention has particular utility in the modulation of processing of IL-1β for the treatment of rheumatoid arthritis. Levels of IL-1β are known to be elevated in the syncvial fluid of patients with the disease. Additionally, IL-1β stimulates the synthesis of enzymes believed to be involved in inflammation, such as collagenase and PLA2, and produces joint destruction which is very similar to rheumatoid arthritis following intra-articular injection in animals.

In the practice of this invention an effective amount of a compound of the invention or a pharmaceutical composition thereof is administered to the subject in need of, or desiring, such treatment. These compounds or compositions may be administered by any of a variety of routes depending upon the specific end use, including orally, parenterally (including subcutaneous, intraarticular, intramuscular and intravenous administration), rectafly, buccally (including sublingually), transdermally or intranasally. The most suitable route in any given case will depend upon the use, the particular active ingredient, and the subject involved. The compound or composition may also be administered by means of controlled-release, depot implant or injectable formulations as described more fully herein.

In general, for the uses as described in the instant invention, it is expedient to administer the active ingredient in amounts between about 0.1 and 100 mg/kg body weight, most preferably from about 0.1 to 30 mg/kg body weight for human therapy, the active ingredient will be administered preferably in the range of from about 0.1 to about 20–50 mg/kg/day: This administration may be accomplished by a single administration, by distribution over several applications or by slow release in order to achieve the most effective results. When administered as a single dose, administration will most preferably be in the range of from about 0.1 to mg/kg to about 10 mg/kg.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

A further aspect of the present invention relates to pharmaceutical compositions comprising as an active ingredient a compound of the present invention in admixture with a pharmaceutically acceptable, non-toxic carrier. As mentioned above, such compositions may be prepared for use for parenteral (subcutaneous, intraarticular, intramuscular or intravenous) administration, particularly in the form of liquid solutions or suspensions; for oral or buccal administration, particularly in the form of tablets or capsules; or intranasally, particularly in the form of powders, nasal drops or aerosols.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived form fatty acids and a hexitol such as polyoxyethylene sorbitan monooleate, or condensation products of ethylene oxide with partial ester derived form fatty acids and hexitol anhydrides, for example polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxident such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

When administered orally (or rectafly) the compounds will usually be formulated into a unit dosage form such as a tablet, capsule, suppository or cachet. Such formulations typically include a solid, semi-solid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitar monolaurate, methyl hydroxybenzoate, propyl hydroxybenzoate, talc, and magnesium stearate.

Compositions for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginin acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

The compositions may be prepared by any of the methods well-known in the pharmaceutical art, for example as described in *Remington's Pharmaceutical Sciences*, 17th edition, Mack Publishing Company, Easton, Pa., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Examples of vehicles for parenteral administration include water, aqueous vehicles such as saline, Ringer's solution, dextrose solution, and Hank's solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. For oral administration, the formula can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, and the like (See, B. H. Vickery, "LHRH and its Analogs-Contraception and Therapeutic Applications", Pt. 2, B. H. Vickery and J. S. Nester, Eds., MTP Press, Lancaster, UK, 1987).

DETAILED DESCRIPTION OF THE INVENTION

The compounds of this invention were prepared by using the general synthetic methods as described in Schemes 1, 2, 3, and 4. Z-Asparatic acid α-bromomethyl ketone (Scheme 1; Formula 1; Z=benzyloxyoarbonyl) is treated with an alcohol or a carboxylic acid in the presence of KF using DMF as a solvent to give the α-substituted Z-aspartic acid methyl ketches (Formula 2). The preparation of bromide formula 1 and its conversion to compounds of formula 2 is accomplished using the methods as described by A. Krantz, et al. (*Biochemistry,* (1991), 30, 4678–4687). Subsequently, the Z-group is removed to generate an N-terminal amine (Formula 3) under hydrogenolytic conditions. The reagents and conditions typically used to carry out the hydrogenolyic removal of the Z-group are hydrogen gas, ambient temperature and pressure, 5% palladium on carbon as the catalyst in an alcoholic solvent e.g., methanol optionally containing two equivalent of hydrochloric acid. It is not necessary to purify the intermediate free amine (or the hydrochloride salt if hydrochloric acid is used in the hydrogenolysis), though this material needs to be dry and free of alcohol for the subsequent coupling reaction to proceed in good yield. The amine (Formula 3) so obtained is then condensed with the pyrimidine carboxylic acid (Formula 4) to yield intermediates of Formula 5. It is generally necessary to first activate the pyrimidine carboxylic acid as an acid chloride or mixed anhydride and then react it with the free amine (or hydrochloride salt) in the presence of an organic base, e.g., N-methylmorpholine. Alternatively, coupling the pyrimidine carboxylic acid with the intermediate amine is conducted using amide coupling reagents/conditions employed in peptide coupling chemistry ("The Practice of Peptide Synthesis." M. Bodanszky, Springer-Verlag, N.Y., 1984; The Peptides. Vol 1–3, E. Gross and J. Meienhofer, Eds. Academic Press, N.Y., 1981 ). The remaining synthetic transformation to generate the ICE inhibitors is the hydrolysis of the t-butyl ester function. This is conducted by exposing the t-butyl ester (Formula 5) to a 25% solution of trifluoroacetic acid (TFA) in methylene chloride at 25° C. The de-esterification is usually complete with 3 h. Removal of the volatile TFA and organic solvent affords the aspartic acid (Formula 6). The yield of the reaction is quantitative in most instances, providing the t-butyl ester starting material is of high purity. Purification, if required, can be performed by recrystallization or chromatographic techniques which are well know to those skilled in the art. The concentration of TFA may range from 5%–100% and other organic solvents may be used such as chloroform. Also, a solution of three molar anhydrous hydrochloric acid in ethyl acetate may be used in place of the TFA-methylene chloride solution with equal efficiency.

Scheme 2 outlines the synthesis of the aspartyl aldehyde containing pyrimidines. The starting material for their synthesis is the aspartyl semicarbazone (Formula 7). The Z-group is removed via standard hydrogenation conditions to yield the corresponding amine (Formula 8). This is then coupled to the pyrimidine acid (Formula 4) using coupling conditions analogous to those described above. A double de-protection is required to free the beta carboxylic acid (trifluoracetic acid) and the alfa aldehyde (37% aqueous paraformaldehyde, acetic acid, methanol) yielding compounds of Formula 10.

Scheme 3 outlines an alternate synthetic method for introducing $R_1$ groups onto the pyrimidine 5-amino function further enhancing the scope of this invention. Pyrimidines either as their free acids, esters or aspartic acid amides which contain a Z-group (Formula 11) may be subjected to hydrogenolysis conditions (similar to those described above) to yield the corresponding 5-amino pyrimidines (Formula 12). The amine moiety may be reacted with acid chlorides, or activated carboxylic acids (conditions analogous to those used to couple Formula 3 and 4 as described in Scheme 1 above) to afford $R_1$ containing pyrimidines with structural diversity in $R_1$.

Scheme 4 outlines the synthesis of the requisite pyrimidines. The starting materials used are the 3-carboxyethyl pyrimidines with either the N-ally (Formula 13) or N-acetaldehyde dimethyl acetal (Formula 14). Their synthesis can be readily deduced by those in the art employing the reaction conditions presented in the literature (Veale, C. A.; et al, *J. Org. Chem.* (1993), 58, 4490–4493; Gupta, K. A.; et al. *Ind. J. Chem.* B, 21B, 228; Nemeryuk, M. P.; et al. *Collect. Czech. Chem Commun.* (1986), 51,215–233). The ethyl esters are hydrolyzed in the presence of aqueous base (LiOH in $H_2O$-THF or NaOH in $H_2O$-THF) to give the corresponding acids (Formulas 15 and 16). The carboxylic acids in turn are subjected to a Curtius rearrangement (Pfister, J. R.; et al. *Synthesis*, (1983), 38; Radhakrishna, A. S.; et al. *Synthesis*, (1983), 538; Ninomiya, K.; et al; *Tetrahedron*, (1974), 30, 2151) yielding a highly reactive isocyanate (Formula 17 and 18), which is not isolated, but reacted immediately with an alcohol or an amine (see Ninomiya, K. et al. Supra). The overall process provides either a carbamate (isocyanate trapped with an alcohol) or a urea (isocyanate trapped with an amine), as represented by Formulas 19 and 20. At this point the synthesis diverges in that if an N-allyl pyrimidine was used a starting material (Formula 19), the olefin is oxidized with osmium tetroxide/ N-methyl morphofine N-oxide (See, V. VanRheenen; et al. *Tetrahedron Lett.*, (1976), 1973–1976; *Organic Synthesis* Vol 58, p43–51) and sodium or potassium periodate (H. O. House; *Modern Synthetic Reactions*, W. A. Benjamin Inc., Menlo Park, Calif. 1972,353–359) yielding the intermediate aldehyde (Formula 13→Formula 19→Formula 21). Alternatively, if an N-acetaldehyde dimethyl acetal was used as a starting material (Formula 20), the dimethylacetal functionality is treated with dilute acid (aqueous HCl ) liberating intermediate aldehyde (Formula 14→Formula 20→Formula 21). Acids of formula 4 were obtained from aldehydes of formula 21 via sodium or potassium chlorite-mediated oxidation (B. S. Bal; et al. *Tetrahedron*, (1981 ), 37, 2091 ). It should be noted that trapping the isocyanate (formulas 17 and 18) with benzyl alcohol provides intermediate Z-carbamates which ultimately lead to the compound of formula 11 (Scheme 3).

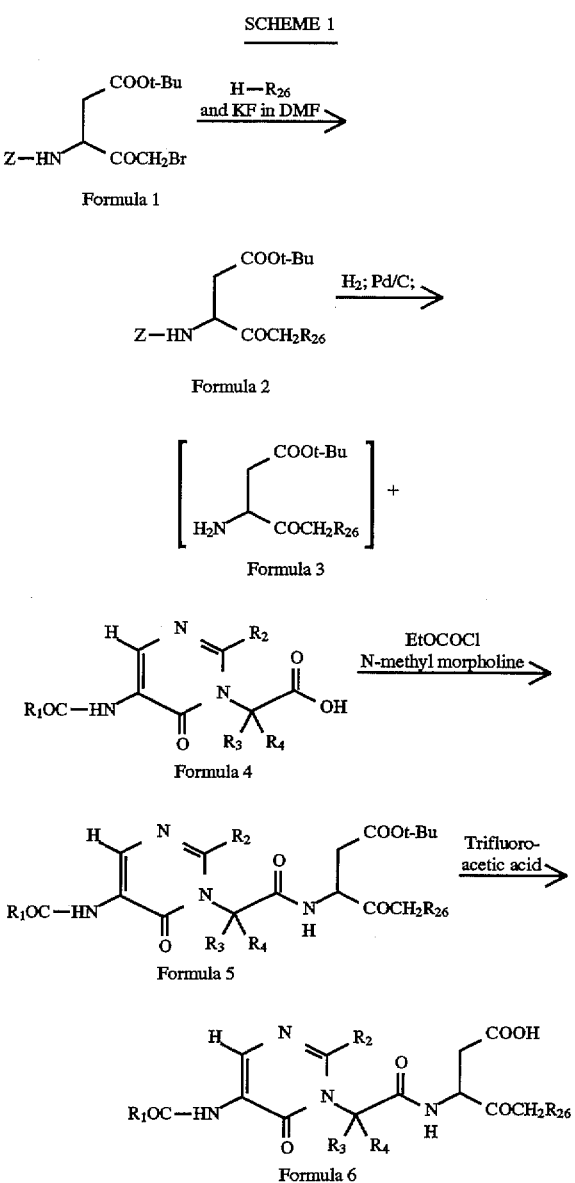

-continued
SCHEME 2
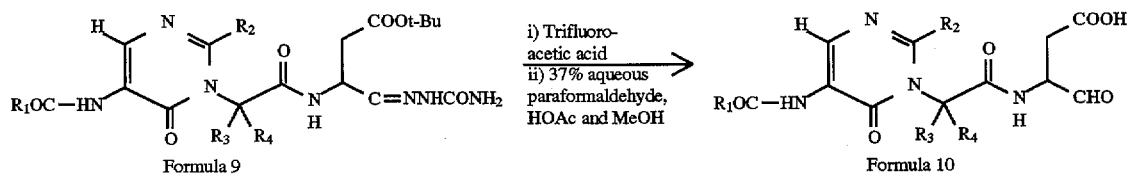
SCHEME 3
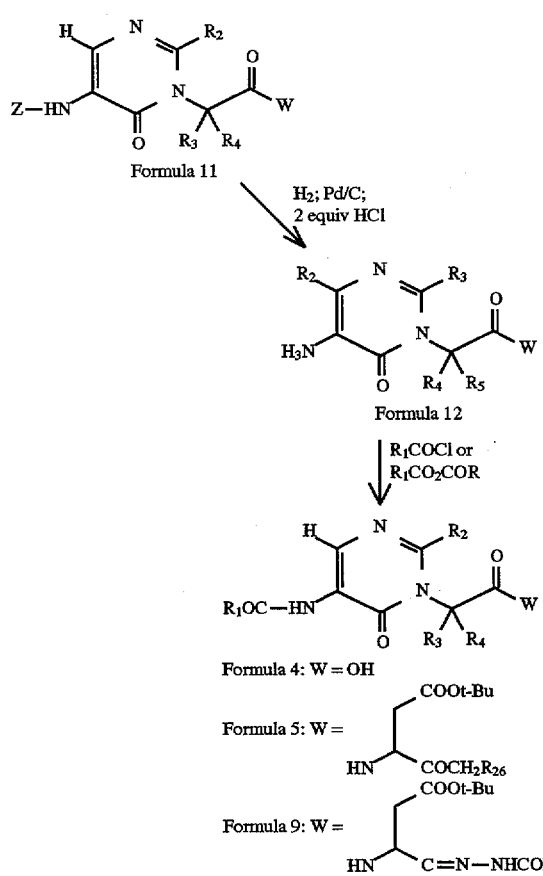
SCHEME 4
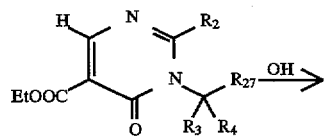
Formula 13: $R_{27} = CH=CH_2$
Formula 14: $R_{27} = CH(OMe)_2$
-continued
SCHEME 4
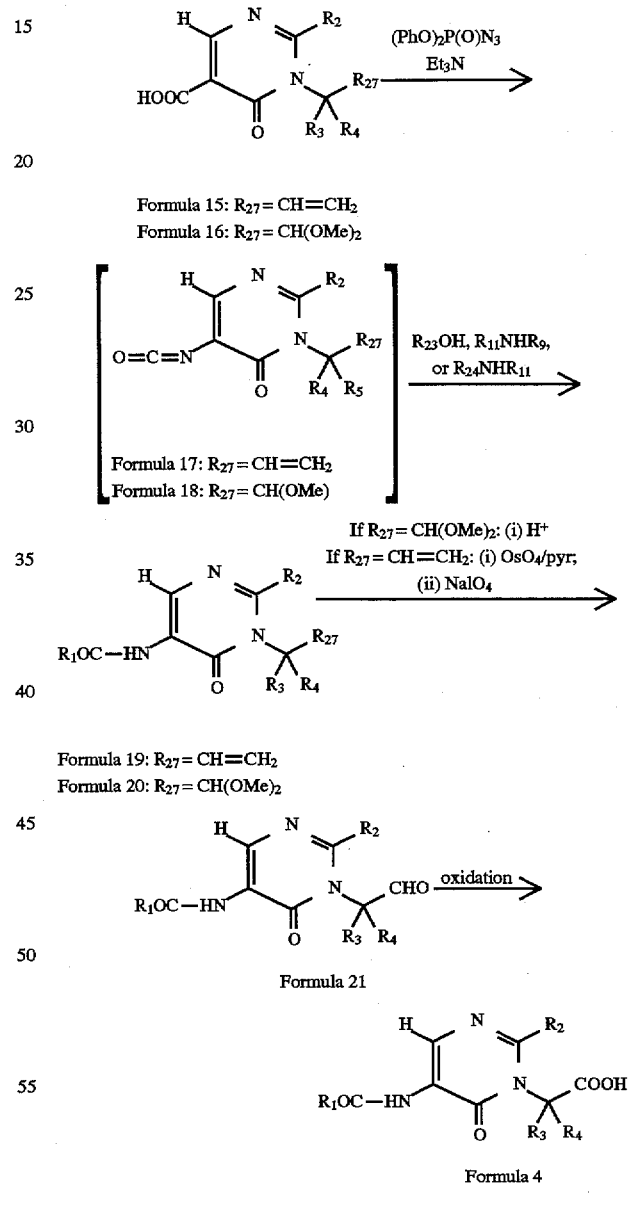
wherein:
$R_1$–$R_4$, $R_9$, $R_{11}$, and $R_{24}$ are as defined in formula (I), Z is defined as the benzyloxycarbonyl group, W is defined as an OH group, a $HNC(H)(CH_2OOtBu)COCH_2R_{26})$ and a $HNC(H)(CH_2COOtBu)C=NNHCONH_2$ moieties, where $R_{26}$ is defined as F, —O(CO)$_{0-1}$-aryl, —OP(O)($R_{14}$)$R_{(15)}$,

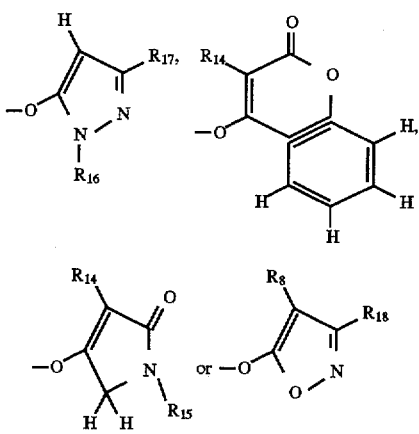

wherein $R_8$, $R_{14}$, $R_{15}$, $R_{16}$, $R_{17}$ and $R_{18}$ are defined as previously.

The following will further illustrate the compounds of the present invention.

EXAMPLE 1

N-[2-(5-Benzyloxycarbonylamino-6-oxo-2-(4-fluorophenyl)-1,6-dihydro-1-pyrimidinyl) acetoyl-L-aspartic acid 2,6-dichlorobenzoyloxymethyl ketone Part A: N-Benzyloxycarbonyl-L-aspartic acid bromomethyl ketone β-tert-butyl ester (0.3 g; 0.76 mM) was dissolved in 12 mL of anhydrous DMF. To this solution was added powdered potassium fluoride (0.11 g; 19 mmol) and 2,6-dichlorobenzoic acid (0.17 g; 0.91 mmol) and the reaction mixture was stirred overnight. The solution was diluted with Et$_2$O and washed with water, aqueous saturated NaHCO$_3$, brine and dried (MgSO$_4$). The ketone so obtained was purified by silica gel chromatography using ethyl acetate/hexane as the eluting solvent ($^1$H NMR (CDCl$_3$) §7.36 (m, 9H), 5.90 (d, 1H), 5.20 (m, 4H), 4.67 (m, 1H), 3.00 and 2.75 (doublet of doublets, 1H each), 1.42 (s, 9H)).
Part B: N-Benzyloxycarbonyl-L-aspartic acid 2,6-dichlorobenzoyloxymethyl ketone β-tert-butyl ester (1.02 g, 2 mmol; Part A above) was dissolved in absolute ethanol (100 mL, 4 mmol) containing 2 equiv. of 6N aqueous HCl (4 mmol) and 10% palladium on carbon (96 mg). The reaction mixture was stirred under an ambient atmosphere of hydrogen gas for approximately I hour (thin layer chromatography [5% MeOH—CH$_2$Cl$_2$] indicated the disappearance of starting material). The solution was filtered and the solvent was removed in vacuo to give L-aspartic acid 2,6-dichlorobenzoyloxymethyl ketone β-tert-butyl ester HCl salt which was used immediately in the subsequent reaction described in Part C.
Part C: A solution of 2-(5-benzyloxycarbonylamino-6-oxo-2-(4-fluorophenyl)-1, 6-dihydro-1-pyrimidinyl) acetic acid (771 mg, 2.05 mmol) in CH$_2$Cl$_2$ (10 mL) was cooled to –20° C. and isobutylchloroformate (0.28 mL, 2.05 mmol) and N-methylmorpholine (0.23 mL, 2.05 mmol) were added sequentially. The reaction mixture was stirred for 15 minutes and a solution of aspartic acid 2,6-dichlorobenzoyloxy methyl ketone β-tert-butyl ester HCl salt (prepared in Part B above) was added followed by a second addition of N-methyl morpholine (0.23 mL, 2.05 mmol). The reaction mixture was stirred for 30 minutes and then was diluted with EtOAc, washed with water, aqueous saturated NaHCO$_3$, brine and dried (MgSO$_4$). The solvents were removed in vacuo and the product purified by silica gel chromatography using 40% EtOAc-hexane as eluent to give N-[2-(5-benzyloxycarbonylamino-6-oxo-2-(4-fluorophenyl-)1, 6-dihydro-1-pyrimidinyl)acetoyl]-L-aspartic acid 2,6-dichlorobenzoyloxymethyl ketone β-tert-butyl ester (1.2 g; 80%).
Part D: A solution of N-[2-(5-benzyloxycarbonylamino-6-oxo-2-(4-fluorophenyl)-1, 6-dihydro-1-pyrimidinyl)acetoyl] -L-aspartic acid 2,6-dichlorobenzoyloxymethyl ketone β-tert-butyl ester (Part C above) in methylene chloride containing 25% v/v trifluoroacetic acid (20 mL) was stirred for 2 hours at 0° C. The solvent was removed in vacuo and the residue was purified by silica gel chromatography to give analytically pure N-[2-(5-benzyloxycarbonylamino-6-oxo-2-(4-fluorophenyl)-1,6-dihydro-1-pyrimidinyl) acetoyl]-L-aspartic acid 2,6-dichlorobenzoyloxymethyl ketone low resolution mass spectrum: m/z=699 (M+H).

EXAMPLE 2

N-[2-(5-Thiomethylbenzoylamino-6-oxo-2-(4-fluorophenyl)-1,6-dihyro-1-pyrimidinyl) acetoyl]L-aspartic acid 2,6-dichlorobenzoyloxymethyl ketone
Part A: N-[2-(5-Benzyloxycarbonylamino-6-oxo-2-(4-fluorophenyl)-1,6-dihydro-1-pydmidinyl) acetoyl]-L-aspartic acid 5-(1-(4-chlorophenyl)-3-trifluoromethyl) pyrazoloxymethyl ketone β-tert-butyl ester (2.5 g, 3.0 mmol) was dissolved in absolute ethanol (100 mL, 4 mmol) containing 2 equiv of 6N aqueous HCl. The solution was degassed with nitrogen and 10% palladium on carbon was added (300 mg). The reaction mixture was stirred under an ambient atmosphere of hydrogen gas for approximately 5 h (thin layer chromatography [50% EtOAc—hexane: Rf starting material=0.5; R$_f$ of product=0.0] indicated the disappearance of starting material). The solution was filtered and the solvent was removed in vacuo to give N-[2-(5-amino-6-oxo-2-(4-fluorophenyl)-1, 6-dihydro-1-pyrimidinyl) acetoyl]-L-aspartic acid 5-(1-(4-chlorophenyl)-3-trifluoromethyl) pyrazoloxymethyl ketone β-tert-butyl ester which was azeotroped with toluene and used without further purification in the subsequent reaction described in Part B.
Part B: To a solution of N-[2-(5-amino-6-oxo-2-phenyl-1, 6-dihydro-1-pyrimidinyl)-acetoyl]-L-aspartic acid 5-(1-(4-chlorophenyl)-3-trifluoromethyl)pyrazoloxymethyl ketone β-tert-butyl ester (713 mg, 1.0 mmol prepared in Part A above) in methylene chloride (30 mL) at 5° C. was added 4-thiomethylbenzoyl chloride (279 mg, 1.5 mmol) followed by the addition of N-methylmorpholine (0.5 mL; 4.5 mmol) and 4-N,N-dimethylaminopyridine (10 mg). The reaction mixture was stirred for 2 h at 5° C. and then was allowed to warm to room temperature. The solution was diluted with EtOAc, washed with water, saturated aqueous NaHCO$_3$, brine and dried (MgSO$_4$). The solvents were removed in vacuo. The product was purified by silica gel chromatography using about 30% EtOAc-hexane as eluent to give N-[2-(5-(4-thiomethylbenzoylamino)-6-oxo-2-(4-fluorophenyl)-1,6-dihydro-1-pyrimidinyl) acetoyl]-L-aspartic acid 5-(1-(4-chlorophenyl)-3-trifluoromethyl) pyrazoloxymethyl ketone β-tert-butyl ester in 50% yield.
Part C: N-[2-(5-(4-Thiomethylbenzoylamino-6-oxo-2-(4-fluorophenyl)-1, 6-dihydro-1-pyrimidinyl)acetoyl]-L-aspartic acid 5-(1-(4-chlorophenyl)-3-trifluoromethyl) pyrazoloxymethyl ketone β-tert-butyl ester was converted to its corresponding acid, N-[2-(5-(4-thiobenzoylamino)-6-oxo-2-(4-fluorophenyl)-1,6-dihydro-1-pyrimidinyl) acetoyl]-L-aspartic acid 5-(1-(4-chlorophenyl)-3-trifluoromethyl) pyrazoloxymethyl ketone using the conditions described in Part D of example 1 above.
Mass spectrum: m/z=787 (M+H)

Following the procedure in Schemes 1 and 2, and by analogy with Examples 1 and 2, the following compounds were prepared.

EXAMPLE 3

N-[2-(5-Benzyloxycarbonylamino-6-oxo-2-(4-fluorophenyl)-1,6-dihydro-1-pyrimidinyl) acetoyl]-L-aspartic acid diphenylphosphinoxymethyl ketone Mass spectrum: m/z=727 (M+H)

EXAMPLE 4

N-[2-(5-Benzyloxycarbonylamino-6-oxo-2-(4-fluorophenyl)-1,6-dihydro-1-pyrimidinyl) acetoyl]-L-aspartic acid 5-(1-(4-chlorophenyl)-3-trifluoromethyl) pyrazoloxymethyl ketone Mass spectrum: m/z=771 (M+H)

EXAMPLE 5

N-[2-(5-Benzyloxycarbonylamino-6-oxo-2-(4-fluorophenyl)-1,6-dihydro-1-pyrimidinyl) acetoyl]-L-aspartic acid 5-(3-pheny)coumarinyloxymethyl ketone Mass spectrum: m/z=747 (M+H)

EXAMPLE 6

N-[2-(5-Benzyloxycarbonylamino-6-oxo-2-(4-fluorophenyl)-1,6-dihydro-1-pyrimidinyl) acetoyl]-L-aspartic acid 5-(1-phenyl-3-trifluoromethyl) pyrazoloxymethyl ketone Mass spectrum: m/z=737 (M+H)

EXAMPLE 7

N-[2-(5-Isopropyloxycarbonylamino-6-oxo-2-phenyl-1,6-dihydro-1-pyrimidinyl) acetoyl]-L-aspartic acid 5-(1-phenyl-3-trifluoromethyl) pyrazoloxymethyl ketone Mass spectrum: m/z=671 (M+H)

EXAMPLE 8

N-[2-(5-Benzyloxycarbonylamino-6-oxo-2-(3-pyridinyl)-1,6-dihydro-1-pyrimidinyl) acetoyl]-L-aspartic acid 5-(1-phenyl-3-trifluoromethyl) pyrazoloxymethyl ketone Mass spectrum: m/z=720 (M+H)

EXAMPLE 9

N-[2-(5-Benzyloxycarbonylamino-6-oxo-2-(2-thienyl)-1.6-dihydro-1-pyrimidinyl) acetoyl]-L-aspartic acid 5-(1-phenyl-3-trifluoromethyl) pyrazoloxymethyl ketone Mass spectrum: m/z=725 (M+H)

EXAMPLE 10

N-[2-(5-Benzyloxycarbonylamino-6-oxo-2-methyl-1,6-dihydro-1-pyrimidinyl)acetoyl]-L-aspartic acid 5-(1-phenyl-3-trifluoromethyl)pyrazoloxymethyl ketone Mass spectrum: m/z=657 (M+H)

EXAMPLE 11

N-[2-(5-Benzyloxycarbonylamino-6-oxo-2-(2-thienyl)-1,6-dihydro-1 pyrimidinyl)acetoyl]-L-aspartic acid 5-(1-(2-pyridinyl)-3-trifluoromethyl) pyrazoloxymethyl ketone Mass spectrum: m/z=726 (M+H)

EXAMPLE 12

N-[2-(5-Benzyloxycarbonylamino-6-oxo-2-(2-thienyl)-1,6-dihydro-1-pyrimidinyl)acetoyl-L-aspartic acid 5-(1-(4-chlorophenyl)-3-trifluoromethyl)pyrazoloxymethyl ketone Mass spectrum: m/z=759 (M+H)

EXAMPLE 13

N-[2-(5-Benzyloxycarbonylamino-6-oxo-2-(2-thienyl)-1,6-dihydro-1-pyrimidinyl)acetoyl-L-aspartic acid 2,6-dichlorobenzoyloxymethyl ketone Mass spectrum: m/z=687 (M+H)

EXAMPLE 14

N-[2-(5-Benzyloxycarbonylamino-6-oxo-2-(2-thienyl)-1,6-dihydro-1-pyrimidinyl) acetoyl]-L-aspartic acid aldehyde Mass spectrum: m/z=485 (M+H)

Compounds of the present invention were tested for IL-1β protease inhibition activity according to the following protocols:

In Vitro

Second order rate constants for inactivation were obtained using the enzyme assay described in Dolle, R. E. et al.; *J. Medicinal Chemistry*, (1994), 37, 781.

The compounds in examples 1–13 possess IL-1β protease inhibition (kobs/I were>50,000 $M^{-1}$ $s^{-1}$).

In Vivo

In vivo inhibition ($IC_{50}$) was determined based on Miller et al., "Inhibition of Mature" IL-1β Production in Murine Macrophages and a Murine Model of Inflammation By WIN 67694, An Inhibitor of IL-1β Converting Enzyme, J. Immunol., 1994, 154, 1331, as follows:

Human monocytes were isolated from heparinized leukopheresis units obtained through Biological Specialty Corporation (Lansdale, Pa.). Monocytes were purified by Ficoll-Hupaque (Pharmacia Fine Chemicals, Piscataway, N.J.) gradient centrifugation and more than 95% pure monocyte populations obtained by centrifugal elutriation. The assay was performed on duplicate samples of freshly isolated human monocytes, cultured in suspension at 37° C. and rotated gently in conical bottom polypropylene tubes (Sardstedt Inc., Princeton, N.J.). Human monocytes at a concentration of 5×10⁶ cells/mL were resuspended in 1 mL of RPMI 1640 (a common tissue buffer from M. A. Bioproducts, Walkersville, Md.) containing 1% fetal calf serum (FCS) (HyClone, Logan, UT) and 50 μg/mL gentamycin (Gibco, Grand Island, N.Y.). The cells were treated either with a compound of the invention (i.e. test compound) or with a non-inhibitor (control compound, typically 0.03% DMSO) for 15 minutes and then activated with 0.01% fixed *Staphylococcus aureus* (The Enzyme Center, Malden, Mass.) for 1 hour. The cells were then centrifuged and resuspended in 1 mL of cysteine, methionine-free RPMI media containing 1% dialyzed FCS (Hyclone). The cells were pretreated with a test compound or control compound for 15 minutes after which 0.01% fixed *S. aureus* plus 100 μCi Tran 35-S label (ICN, Irvine, Calif.) was added and the cells incubated at 37° C. for 1 hour. After incubation, mL RPMI containing 1% fetal calf serum. The cells were again pretreated with a test or control compound for 15 minutes and then 0.01% *S. aureus* for 2 hours. At the end of the incubation, cells were centrifuged and supernates saved for immunoprecipitation. Cells were washed once in phosphate buffer saline and then lysed in RIPA, a continuous cell media buffer containing 2 mM phenylmethylsulfonyl fluoride, 10 mM iodoacetate, 1 μg/mL pepstatin A, 1 μg/mL leupeptin and 0.5 TIU aprotinin.

For the immunoprecipitations, an equal volume of 1% dry milk in RIPA buffer plus 50 μL of resuspended protein A sepharose CL-4B (Pharmacia, Piscataway, N.Y.) was added to supernates and 1 mL of 4% dry milk containing protein A sepharose CL-4B to cell lysates and samples rotated for 30 minutes at 4° C. Beads were then centrifuged down, samples transferred to fresh tubes and incubated overnight with 40 μg rabbit anti-human IL-1β polyclonal antibody (Genzyme, Cambridge, Mass.). The IL-1β proteins were then precipitated with 70 μL protein A sepharose, resuspended in 60 μL SDS sample buffer and run on 15% SGD-PAGE gels. Autoradiography was performed on dried gels and the amount of radioactivity (counts per minute, cpm) quantitated using a Betascope 603 analyzer.

Data Analysis

In the monocyte pulse chase assay, each test parameter was run in duplicate. Data was collected from the Beta Scope using a personal computer, then transferred to the VAX system for calculation of mean cpm and standard deviation of the mean. When test compounds were evaluated, the percent inhibition of release of mature IL-1β was calculated as follows:

100×[1−(cells treated with stimuli+test compound−unstimulated cells)/(cells treated with stimuli+control compound−unstimulated cells)]

These % inhibition values were then used to calculate $IC_{50}$ value for each compound. Since the human monocyte pulse chase assay uses primary cells from different donors, each test compound was run in 2–3 separate experiments, using monocytes from 2–3 different donors.

For examples 1,6,7 and 9, the in vivo $IC_{50}$'s ranged from approximately 0.1 to up to approximately 10 μM.

Elastase Inhibition (In Vitro)

Compounds of examples 1, 6 and 7 were examined for their ability to inhibit elastase. The in vitro assay was carried out as described by Cha, *Biochem. Pharmacol.*, (1975), 24, 2177–2185. Examples 1,6 and 7 which are representative of this class of ICE inhibitor, did not inhibit elastase with $IC_{50}$'s≧10 μM.

Having described the invention with reference to its preferred embodiments, it is to be understood that modifications within the scope of the invention will be apparent to those skilled in the art.

What is claimed is:

1. A compound selected from the group consisting of:

N-[2-(5-benzyloxycarbonylamino-6-oxo-2-(4-fluorophenyl)-1, 6-dihydro-1-pyrimidinyl-acetoyl]-L-aspartic acid 2,6-dichlorobenzoyloxymethyl ketone;

N-[2-(5-thiomethyl-benzoylamino-6-oxo-2-(4-fluorophenyl)-1, 6-dihyro-1-pyrimidinyl) acetoyl]-L-aspartic acid 2,6-dichlorobenzoyloxymethyl ketone;

N-[2-(5-benzyloxycarbonylamino-6-oxo-2-(4-fluorophenyl)-1, 6-dihydro-1-pyrimidinyl)acetoyl]-L-aspartic acid diphenylphosphinoxymethyl ketone;

N-[2-(5-benzyloxycarbonylamino-6-oxo-2-(4-fluorophenyl-1, 6-dihydro- 1-pyrimidinyl)acetoyl]-L-aspartic acid 5-(1-(4-chlorophenyl)-3-trifluoromethyl) pyrazoloxymethyl ketone N-[2-(5-benzyloxycarbonylamino-6-oxo-2-(4-fluorophenyl)-1, 6-dihydro-1-pyrimidinyl)acetoyl]-L-aspartic acid 5-(3-pheny)coumarinyloxymethyl ketone;

N-[2-(5-benzyloxycarbonylamino-6-oxo-2-(4-fluorophenyl)-1, 6-dihydro-1-pyrimidinyl)acetoyl]-L-aspartic acid 5-(1-phenyl-3-fluoromethyl)-pyrazoloxymethyl ketone;

N-[2-(5-isopropyloxycarbonylamino-6-oxo-2-phenyl-1, 6-dihydro-1-pyrimidinyl) acetoyl]-L-aspartic acid 5-(1-phenyl-3-trifluoromethyl)pyrazoloxymethyl ketone;

N-[2-(5-benzyloxycarbonylamino-6-oxo-2-(3-pyridinyl)-1, 6-dihydro-1-pyrimidinyl)acetoyl]-L-aspartic acid 5-(1-phenyl-3-trifluoromethyl)pyrazoloxymethyl ketone;

N-[2-(5-benzyloxycarbonylamino-6-oxo-2-(2-thienyl)-1, 6-dihydro-1-pyrimidinyl) acetoyl]-L-aspartic acid 5-(1-phenyl-3-trifluoromethyl)pyrazoloxymethyl ketone;

N-[2-(5-benzyloxycarbonylamino-6-oxo-2-methyl-1, 6-dihydro-1-pyrimidinyl)-acetoyl]-L-aspartic acid 5-(1-phenyl-3-trifluoromethyl)pyrazoloxymethyl ketone;

N-[2-(5-benzyloxycarbonylamino-6-oxo-2-(2-thienyl)-1, 6-dihydro-1-pyrimidinyl) acetoyl]-L-aspartic acid 5-(1-(2-pyridinyl)-3-trifluoromethyl)pyrazoloxymethyl ketone;

N-[2-(5-benzyloxycarbonylamino-6-oxo-2-(2-thienyl)-1, 6-dihydro-1-pyrimidinyl) acetoyl]-L-aspartic acid 5-(1-(4-chlorophenyl-3-trifluoromethyl) pyrazoloxymethyl ketone;

N-[2-(5-benzyloxycarbonylamino-6-oxo-2-(2-thienyl)-1, 6-dihydro-1-pyrimidinyl) acetoyl]-L-aspartic acid 2,6-dichlorobenzoyloxymethyl ketone; and N-[2-(5-benzyloxycarbonylamino-6-oxo-2-(2-thienyl)-1, 6-dihydro-1-pyrimidinyl) acetoyl]-L-aspartic acid aldehyde.

2. A pharmaceutical composition for inhibiting interleukin-1β protease comprising a compound selected from the group consisting of:

N-[2-(5-benzyloxycarbonylamino-6-oxo-2-(4-fluorophenyl)-1,6-dihydro-1-pyrimidinyl) acetoyl]-L-aspartic acid 2,6-dichlorobenzoyloxymethyl ketone;

N-[2-(5-thiomethylbenzoylamino-6-oxo-2-(4-fluorophenyl)-1,6-dihydro-1-pyrimidinyl) acetoyl]-L-aspartic acid 2,6-dichlorobenzoyloxymethyl ketone;

N-[2-(5-benzyloxycarbonylamino-6-oxo-2-(4-fluorophenyl)-1,6-dihydro-1-pyrimidinyl) acetoyl]-L-aspartic acid diphenylphosphinoxymethyl ketone;

N-[2-(5-benzyloxycarbonylamino-6-oxo-2-(4-fluorophenyl-1,6-dihydro-1-pyrimidinyl) acetoyl]-L-aspartic acid 5-(1-(4-chlorophenyl)-3-trifluoromethyl) pyrazoloxymethyl ketone;

N-[2-(5-benzyloxycarbonylamino-6-oxo-2-(4-fluorophenyl)-1, 6-dihydro-1-pyrimidinyl)-acetoyl]-L-aspartic acid 5-(3-pheny)coumarinyloxymethyl ketone;

N-[2-(5-benzyloxycarbonylamino-6-oxo-2-(4-fluorophenyl)-1,6-dihydro-1-pyrimidinyl) acetoyl]-L-aspartic acid 5-(1-phenyl-3-trifluoromethyl) pyrazoloxymethyl ketone;

N-[2-(5-isopropyloxycarbonylamino-6-oxo-2-phenyl-1,
  6-dihydro-1-pyrimidinyl) acetoyl]-L-aspartic acid
  5-(1-phenyl-3-trifluoromethyl)pyrazoloxymethyl
  ketone;

N-[2-(5-benzyloxycarbonylamino-6-oxo-2-(3-pyridinyl)-
  1,6-dihydro-1-pyrimidinyl) acetoyl]-L-aspartic acid
  5-(1-phenyl-3-trifluoromethyl)pyrazoloxymethyl
  ketone;

N-[2-(5-benzyloxycarbonylamino-6-oxo-2-(2-thienyl)-1,
  6-dihydro-1-pyrimidinyl) acetoyl]-L-aspartic acid
  5-(1-phenyl-3-trifluoromethyl)pyrazoloxymethyl
  ketone;

N-[2-(5-benzyloxycarbonylamino-6-oxo-2-methyl-1,6-
  dihydro-1-pyrimidinyl) acetoyl]-L-aspartic acid 5-(1-
  phenyl-3-trifluoromethyl)pyrazoloxymethyl ketone;

N-[2-(5-benzyloxycarbonylamino-6-oxo-2-(2-thienyl)-1,
  6-dihydro-1-pyrimidinyl) acetoyl]-1,6-dihydro-1-
  pyrimidinyl)acetoyl]-L-aspartic acid 5-(1-(2-pyridinyl)
  -3-trifluoromethyl)pyrazoloxymethyl ketone;

N-[2-(5-benzyloxycarbonylamino-6-oxo-2-(2-thienyl)-1,
  6-dihydro-1-pyrimidinyl) acetoyl-L-aspartic acid 5-(1-
  (4-chlorophenyl)-3-trifluoromethyl)pyrazoloxymethyl
  ketone;

N-[2-(5-benzyloxycarbonylamino-6-oxo-2-(2-thienyl)-L-
  aspartic acid 2, 6-dichlorobenzoyloxymethyl ketone;
  and N-[2-(5-benzyloxycarbonyl-amino-6-oxo-2-(2-thienyl)-
  1,6-dihydro-1-pyrimidinyl) acetoyl]-L-aspartic acid
  aldehyde.

\* \* \* \* \*